(12) United States Patent
Henes et al.

(10) Patent No.: US 7,891,251 B2
(45) Date of Patent: Feb. 22, 2011

(54) DEVICE FOR MEASURING PRESSURE

(75) Inventors: Rudolf Henes, Schaffhausen (CH);
Walter Pauli, Blumberg (DE); Andreas Bayer, Gottmalingen (DE); Beat Krattiger, Beringen (CH)

(73) Assignee: Storz Endoskop Produktions GmbH (DE)

( * ) Notice: Subject to any disclaimer, the term of this patent is extended or adjusted under 35 U.S.C. 154(b) by 92 days.

(21) Appl. No.: 12/469,301

(22) Filed: May 20, 2009

(65) Prior Publication Data

US 2009/0288494 A1   Nov. 26, 2009

(30) Foreign Application Priority Data

May 20, 2008   (DE)   ..................... 10 2008 024 396

(51) Int. Cl.
*G01L 7/00* (2006.01)
(52) U.S. Cl. ........................................ 73/706
(58) Field of Classification Search ................. None
See application file for complete search history.

(56) References Cited

U.S. PATENT DOCUMENTS

| 4,185,641 | A | * | 1/1980 | Minior et al. | ............... 600/488 |
|---|---|---|---|---|---|
| 6,880,404 | B2 | | 4/2005 | Uberreiter | |
| 2004/0050168 | A1 | * | 3/2004 | Uberreiter | ..................... 73/706 |
| 2009/0007683 | A1 | * | 1/2009 | Kaneko et al. | ................ 73/728 |

FOREIGN PATENT DOCUMENTS

| DE | 4219889 A1 | 12/1993 |
|---|---|---|
| DE | 10329159 A1 | 1/2005 |
| DE | 102007000200 A1 | 10/2008 |
| EP | 1813300 A1 | 1/2007 |

OTHER PUBLICATIONS

German Office Action; Application No. 102008024396.5-52; Jan. 30, 2009 (3 pages).

* cited by examiner

*Primary Examiner*—Andre J Allen
(74) *Attorney, Agent, or Firm*—St. Onge Steward Johnston & Reens LLC

(57) ABSTRACT

A device for measuring pressure in a fluid line, with a fluid chamber, which is connected with the fluid line so as to allow flowthrough, and with a transducer, characterized in that the fluid chamber includes an opening to a branch line and in the branch line of the fluid chamber at least one end of a transmission element is inserted. The transmission element forms a power-locking connection between the fluid chamber and the transducer and the transmission element is suited for transmitting the fluid pressure to the transducer. This device proves to be especially precise and is easily sterilized.

16 Claims, 4 Drawing Sheets

DEVICE FOR MEASURING PRESSURE

CROSS-REFERENCE TO RELATED APPLICATIONS

The present application claims priority of German patent application No. 10 2008 024 396.5 filed on May 20, 2008.

FIELD OF THE INVENTION

The invention relates to a device for measuring pressure in a fluid line, which includes a fluid chamber, which is connected with the fluid line so as to allow flowthrough, and a transducer.

BACKGROUND OF THE INVENTION

Devices of the aforesaid type are disclosed, for instance, in DE 42 19 889 A1, EP 1 8013 300 A1, and U.S. Pat. No. 6,880,404 B2.

Such devices make possible the measurement of pressure in fluid lines, in particular in synthetic hoses that are used in medical technology in extracorporeal hose systems or hose assemblies for conducting or transporting fluids.

Fluids may include, for instance, medical irrigation fluids like salt solutions used for cleansing the interior of a body cavity or of a joint. Other possibilities of fluids include gasses or gas mixtures that, for instance, are used for insufflation of the abdominal cavity in the relation to a laparoscopic procedure.

The hose system or hose assembly is connected with a medical device, for instance a roller pump or insufflator, to conduct the fluid.

A hose assembly can comprise the following components:
  a connection to a supply reservoir, in which the fluid to be conducted is stored, for instance a sack for liquids
  a hose segment, composed of more resistant synthetic material, which is inserted into the medical device
  additional synthetic hoses, used for instance for conducting the fluid in or out
  connector elements (connectors) for the hose segment and for conducting the fluid in or out
  a connection to a trocar of an endoscope Parts of the hose assembly or the entire hose assembly can be configured as one-time disposable articles or as reusable items.

The hose assembly must be sterile because it is connected to an instrument whose distal end is to be inserted into a patient's body cavity. Therefore no measurement devices connected to the hose assembly must be allowed to affect the sterility of the interior of the hose assembly. This requirement can be fulfilled by ensuring that the complete measurement device is in sterile condition. However, this involves the problem of having to ensure the sterility of the entire signal transmission pathway from the interior of the hose assembly all the way to the recording unit. In addition, said recording unit itself, for instance a transducer, must be of sterile configuration. This leads to the disadvantage of increased production and operating costs for the measurement device.

Alternatively, the signal transmission pathway contains an interface between a sterile part and a part that is not required to be of sterile configuration. The sterilize part of the signal transmission pathway picks up the signal that is to be measured, for instance the fluid pressure, in the interior of the hose assembly and conducts it onward to the interface. Thanks to the interface, the interior of the hose assembly is sterile and isolated from the environment. The recording unit and the part of the signal transmission path between the interface and the recording unit can be of non-sterile configuration. Consequently, substantial savings in cost and complex arrangements can be achieved, because a semiconductor pressure sensor, for instance, is not required to be of designed and built so that it is autoclavable. The problem with this alternative approach consists in providing an appropriate interface which ensures good signal transmission and seals off the sterile interior of the hose assembly. The interface must constitute an essentially impenetrable barrier for pathogenic germs.

The aforementioned documents U.S. Pat. No. 6,880,404 B2, DE 42 19 889 A1, and EP 1 813 300 A1, disclose devices that comprise a fluid chamber. The fluid chamber is configured as a flow-through chamber, which is connected at both the fluid ingress end and the fluid egress end with a fluid line that can be part of a hose assembly. The fluid chamber is provided with a wall that is configured as a flexible membrane or shaped from elastic material.

The disadvantage of these embodiments is that the fluid chamber cannot be constructed of a material or in a production stage, which for instance is possible for an injection moulded piece of synthetic material.

In the device disclosed in U.S. Pat. No. 6,880,404 B2 another membrane is present, flush with the wall of the fluid chamber, and is a part of a housing that comprises a transducer. As a result, the measuring is mainly made possible both by positive pressures (excess pressure with respect to the ambient pressure) and by negative pressures (low pressure with respect to the ambient pressure).

The disadvantage of this embodiment, however, is that no hydraulically rigid power lock is provided by the transducer between the elastic wall of the fluid chamber and the membrane of the transducer housing. The recorded pressure in areas close to the ambient pressure is not linearly dependent on the pressure at which the fluid line is impacted. Consequently, precise measurements of negative or positive pressures are impossible in areas of the ambient pressure.

In the devices disclosed in DE 42 19 889 A1 and EP 1 8013 300 A1, the wall is positioned, separated by an intermediate space, opposite a transducer. The intermediate space can be evacuated, aerated, or drained of air, so that the wall and the transducer can be brought into power-locking connection. This makes possible a precise measurement of positive pressures and negative pressures in the area of the ambient pressure.

The disadvantage of this embodiment is that the intermediate space impacted with a vacuum or with low pressure, its insulations and feeder lines are difficult to keep clean. In addition, from the adjacent vacuum from the non-sterile environment, impurities can be suctioned into the intermediate space and thus endanger the sterility of the interior of the hose assembly.

It is the object of the present invention to improve a device for measuring pressure of the aforementioned type, which is intended in particular for use in minimally invasive surgery, in such a way that one of the aforementioned disadvantages of the known devices is avoided. Precise measurement of the pressure should become possible in areas close to the ambient pressure. The cleanliness of the device and the sterility of the fluid should be ensured in appropriate ways.

SUMMARY OF THE INVENTION

This object is achieved according to the invention with a device for measuring pressure of the aforementioned type in that the fluid chamber comprises an opening to a branch line and at least one end of a transmission element is inserted into the branch line of the fluid chamber and the transmission element forms a power-locked connection between the fluid chamber and the transducer, and the transmission element is appropriate for transmitting the fluid pressure onto the transducer.

The fluid pressure that is present in the fluid chamber is registered and conducted onward to an interface by means of the transmission element. Said transmission element constitutes a mechanically shaped signal transmission path that conducts the pressure in the fluid chamber onward to the interface. This part of the signal transmission path is of sterile configuration. The interface produces a power-locked connection between the transmission element and the transducer, whereby it becomes possible for pressure to be recorded by the transducer. The interface provides an essentially sterile insulation for the interior of the fluid chamber.

Thus, in surprisingly simple manner, it is possible to bypass the previously existing necessity for an intermediate space that is a vacuum. This fact substantially simplifies the construction. Fewer components are required, because, for instance, the necessity for additional insulating rings, or for lines leading in and out, has ceased. In addition there is no need, for instance, for a pump to produce the low pressure. The result is a dramatic price reduction for the device along with clearly superior cleansing properties and easier handling.

The opening to the branch line of the fluid chamber can be made in the wall of the fluid chamber aligned with the flow direction of the fluid. A transmission element, in particular at least one end of a transmission element, is installed in the branch line of the fluid chamber, and said element makes it possible to transcribe the pressure acting on the fluid line. There is the greatest possible freedom of selection for the material, type, and structure of the transmission element, which ensures a power-locking connection between the fluid chamber and the transducer. Especially advantageous configurations of the invention are treated in the subsidiary claims.

The power-locking connection enables an essentially undistorted transmission of the pressure from the fluid line to the transducer by way of the connected fluid chamber and the transmission element. The transducer records the value of the pressure in the fluid line, in some cases after a calibration.

In a preferred embodiment of the inventive device, the fluid chamber is configured as a flow-through chamber. The flow-through chamber can be part of a synthetic hose that is part of the aforementioned hose assembly, in the same manner as is used in endoscopy.

This provision has the advantage that the pressure prevailing in the fluid chamber corresponds essentially to the pressure acting on the fluid line. Distortion of the pressure measurements by unfavorable hydrodynamic flow conditions, which can easily occur in the vicinity of depressions or hollow spaces and can contribute to the formation of whirlpool effects and turbulent flow, can be efficiently reduced or prevented. In a fluid chamber, for instance, that comprises only a connection for conducting fluid in and out, narrowing or congestion of the flow can occur, with the result that pressure of fluid in the fluid chamber does not correspond to the fluid pressure in the fluid line.

In another preferred embodiment, the fluid ingress end of the fluid chamber, which is configured as a flow-through chamber, and the fluid egress end of the fluid chamber are dissolubly connected with the fluid line.

This provision has the advantage that the fluid chamber can be produced as a component or a set of components that are replaceable. Consequently, the fluid chamber an be produced from injection moulded pieces, which are joined in flush-fitting connection by means of an ultrasound soldering process. Thanks to this practicable production method, high production output can be achieved at low unit cost.

Another advantage of this provision can be seen in the fact that the fluid chamber can take the form of an inexpensive disposable product, produced under sterile conditions, and can be discarded after use, avoiding complex and costly sterilization procedures. Thus the fluid chamber can be marketed as a component of a hose assembly, in particular as a connecting element (connector) of the hose segment that is inserted into a roller pump and for the supply and draining lines for the fluid that are usually made of synthetic hoses. In this way the operating room can be maintained optimally in sterile condition.

Alternatively, the fluid chamber can be produced in reusable form so that it can be steam-sterilized or autoclaved. Because of the removable fluid line, the fluid chamber is suited for marketing as a component of a medical device, for instance of a roller pump for conducting irrigation fluids to cleanse joints in anthroscopy. The related hose assembly can be marketed with the corresponding hoses as a separate product for affixing to the fluid chamber of the roller pump.

In another especially preferred embodiment, the transmission element is subjected to pre-tensing.

Pre-tensing, in the terms of this invention, means that the transducer records a basically constant pressure, greater than zero, that is generated by the transmission element and is conveyed onward to the transducer.

This provision advantageously improves the registering of negative pressures and allows especially more precise measurements of dynamic or static pressure areas in the vicinity of the ambient pressure and improves the linear dependency of the recorded pressure on the pressure of the fluid in the fluid chamber.

An especially advantageous pre-tensing with appropriate embodiments occurs in the range of 0.5 bar to 1.5 bar. With especially advantageous embodiments, the pre-tensing is at approximately 1 bar.

The device can be calibrated, for instance in an essentially unfilled fluid line or one impacted with a vacuum, by means of the positive pressure that is recorded by the transducer and by means of the transmission element impacted with pre-tensing.

An additional advantage of this provision can be seen in the fact that the transducer can be configured as a high-pressure sensor that is suited only for recording positive pressures and is available at reasonable cost in the marketplace, for instance as piezo-resistive or piezo-electric pressure sensors.

Housings for transducers can comprise a filling, such as a gel or silicon filling for instance, that can be surrounded by a membrane. The filling serves to retransmit the pressure of the membrane of the transducer housing to the transducer. It can be the last member of the pressure transmission chain that, starting from the transmission element that scans the fluid pressure, transmits the pressure to the transducer. The pre-tensing that affects the housing of the transducer leads to an essentially homogeneous pressure distribution in the filler, avoiding any evasion or nonhomogeneous distribution of the filling. This can advantageously avoid drifting of the pressures or pressure measurements that summarily arise, approximately proportionately, from the pre-tensing and the fluid pressure.

In addition, the invention allows the capturing of the pre-tensing by the transducer, the testing of the correct structure of the connecting elements (connectors) of the hose assembly, the control of the process of filling the hose assembly with the fluid, monitoring of the control of the medical device, calibration of the pressure close to the application, as well as recording of parameters for regulating the medical device, which can be configured in particular as a roller pump.

In an additional preferred embodiment of the invention, the pre-tensing that affects the transmission element is configured so that it can be adjusted.

This provision has the advantage that the value of the positive pressure recorded by the transducer and generated by the pre-tensed transmission element, can be adjusted specifically by situation to the concrete medical application, increasing the patient's safety in the context of the medical application that is taking place.

In another preferred embodiment of the invention, the transmission element is configured in the form of a piston.

This provision allows an especially simple and in some cases automated assembly of the inventive device, because the end of a piston-shaped transmission element can be inserted especially easily into the opening of the fluid chamber in the course of the assembly process.

The piston-shaped transmission element can comprise bore-holes or perforations. These allow the fluid to flow through the transmission element, which in especially advantageous manner causes a homogeneous distribution of the fluid and the fluid pressure around the transmission element. This results in increased precision in recording fluid pressure by the transducer, thus contributing to the safety of the clinical application.

In another preferred embodiment of the invention, the transmission element is equipped with at least one spring arrangement or at least one magnetic device, both of which are suitable for generating the pre-tensing.

This provision has the advantage that spring arrangements or magnetic arrangements of the greatest range of size and shapes, and with a great variety of spring rates or magnetic sizes, respectively, can be produced, obtained in the marketplace at favorable cost, and easily integrated. Magnetic assemblies are free of friction, thereby preventing possible contaminations by abrasion that can endanger the sterility of the device.

The transmission element is preferably configured as a single unit.

This has the advantage that one-piece components can easily be produced from the greatest variety of materials and adapted to given shapes or geometric configuration, because the most varied processing and production methods can be used, for instance grinding, milling, injection moulding, and the like. A component of unit design, executed as a single piece, is especially easy to sterilize because no fissures or hollow areas are found between individual parts.

In an alternative configuration of the invention, the transmission element is configured in several parts.

This provision has the advantage that the transmission element can more easily be adapted to the functions to be performed—scanning the pressure, producing and transmitting a pre-tensing, and configuring a power-locking connection. Thus, the transmission element can be reshapable, for instance, or can comprise movable parts such as s spring or a piston ram. In addition it allows the exchange of defective parts, so that maintenance tasks can be more flexibly arranged.

In another preferred embodiment of the invention, the transmission element is configured so that it is replaceable.

The advantage of this measure is that in case of defects of the transmission element, a repair of the device can be performed through simple exchange of the transmission element without the need to replace the entire inventive device.

In an additional preferred embodiment of the invention, the end of the transmission element facing the transducer is surrounded by a membrane so that a fluid-tight lock of the branch line of the fluid chamber is configured with the end of the transmission element facing the transducer.

This provision has the advantage of increasing or guaranteeing the fluid-proof insulation of the fluid line and of preventing dripping or degassing of the fluid.

In addition, the interior of the fluid chamber or of the fluid line is isolated from the additional surroundings and sterile, increasing safety. As a result it is possible also to use a nonsterile transducer, for cost savings and simplicity in producing the device, a process that otherwise would require costly sterilization procedures for the transducer.

In addition there is increased precision in registering pressure, because the membrane applies pressure evenly to the transducer over its entire surface, which is in power-locking connection with the membrane.

In another preferred embodiment of the invention, the branch line of the fluid chamber, in which the end of the transmission element is inserted, is closed off fluid-tight by an insulating ring or a membrane This provision increases the insulation and sterility of the device in an especially simple manner.

In another preferred embodiment of the invention, the end of the transmission element that is inserted into the branch line of the fluid chamber is mounted so that it can slide by means of silicon oil and, by means of an insulating element, forms a fluid-tight lock for the opening.

This provision has the advantage that through the gliding mounting of the transmission element, the transmission of pressure to the transducer becomes especially easy and efficient without endangering the insulation and sterility of the fluid chamber.

In another preferred embodiment of the invention, the device comprises several transmission elements and several transducers as well as a fluid chamber with several openings to several branch lines.

This arrangement has the advantage that several transducers can be applied for mutual monitoring. Consequently additional control circuits, for instance, can be constructed, which can be applied to increase the safety of the device.

In addition, the measurement reinforcer and the temperature compensation for the several transducers can be arranged in a switching layout on a print or a circuit board. As a result, considerable cost advantages and space economies can be realized.

In another preferred embodiment of the invention, at least one membrane is provided, which forms a fluid-tight lock of the several branch lines of the fluid chamber and the lock keeps the interior of the fluid chamber sterile.

This arrangement has the advantage that the several branch lines of the fluid chamber can be kept insulated and sterile by, for instance, only a single membrane or a single double membrane. As a result the number of components of the device can be kept low, making production more cost-effective and simpler. A low number of components contributes to reducing the probability of the device malfunctioning.

In another preferred embodiment of the invention, the outer walls of the fluid chamber comprise at least one recess that is suited as a positioning aid.

This arrangement has the advantage that the at least one recess in the outer walls of the fluid chamber, which can be configured for instance as a lateral groove or grooves that simplify placement and dismantling of the fluid chamber.

Consequently, the fluid chamber can be used, for instance, as a connecting element (connector) of a hose assembly that can thus be placed more precisely in a medical device, in particular a roller pump, at the intended position because of the precisely configured depth. As a result, exchanging the house assembly, for instance, can be simpler and more rapid, so that work time and costs are economized with service personnel who are entrusted with the corresponding tasks of maintenance and operation of the medial device. In addition the sterility in the operating area can be ensured more easily.

In another preferred embodiment of the invention, the fluid chamber locked by a leer in the housing of a medical device, so that the lever impacts the fluid chamber with a force that corresponds to a multiple of the sum of the pre-tensing and pressure of the fluid.

This measure has the advantage that the fluid chamber is brought into a power-locking connection with the housing of the medical device. The transducer can be positioned in the housing of a medical device. Because of the power lock, configured by the lever between the fluid chamber and the housing, it becomes possible in especially advantageous manner to record the fluid pressure in the fluid chamber. This provision allows the replacement of the fluid chamber, which can be configured as dissoluble from the fluid line, for instance as part of a hose assembly.

It is understood that the foregoing named characteristics, and those yet to be presented, can be applied not just in the indicated combinations but also in other combinations or in isolation, without leaving the framework of the present invention.

The invention is described and explained hereafter using an especially preferred embodiment in connection with the appended illustrations.

DETAILED DESCRIPTION OF THE INVENTION

Figure 1:
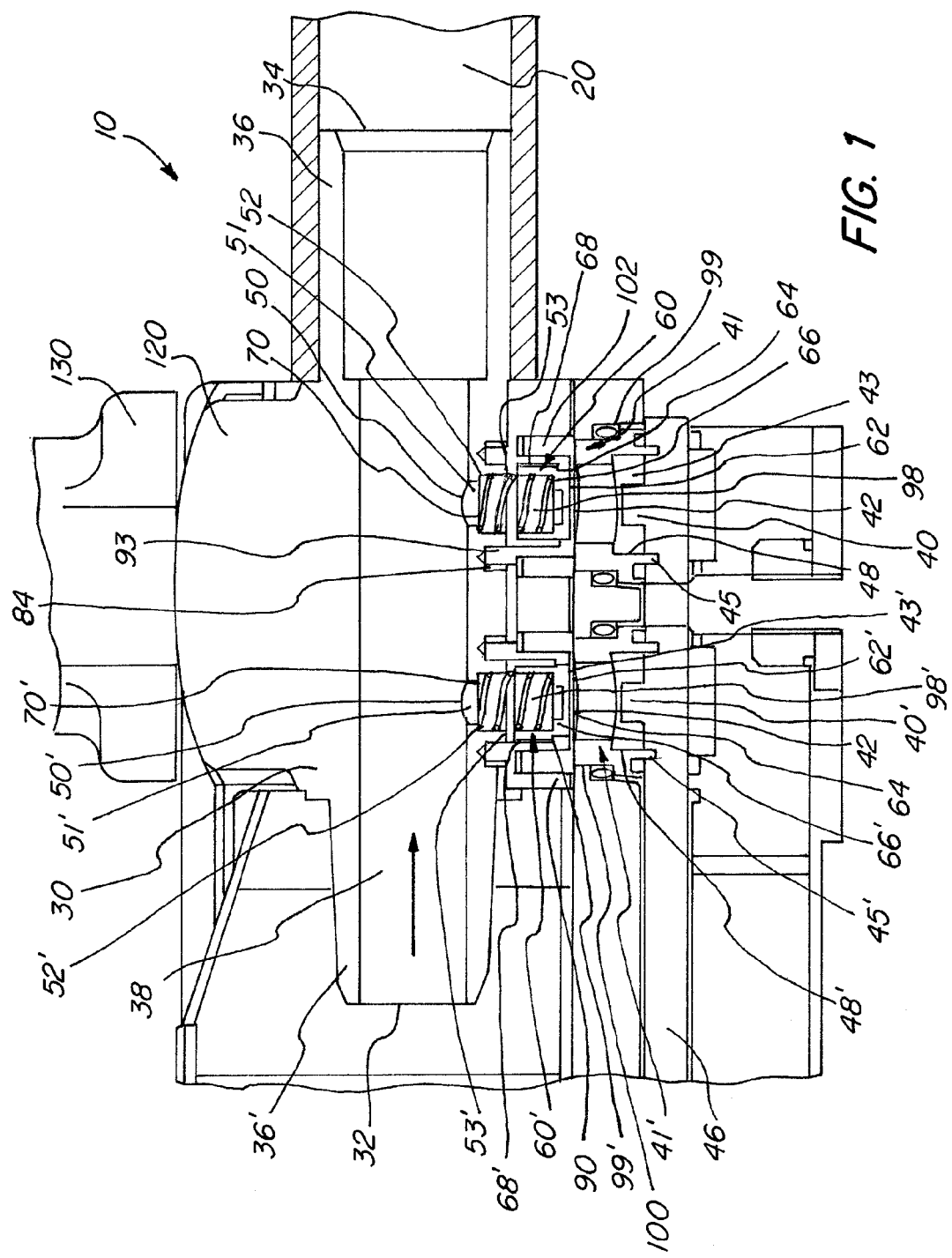
FIG. 1 shows a schematic depiction of an inventive device in longitudinal section.
Figure 2:
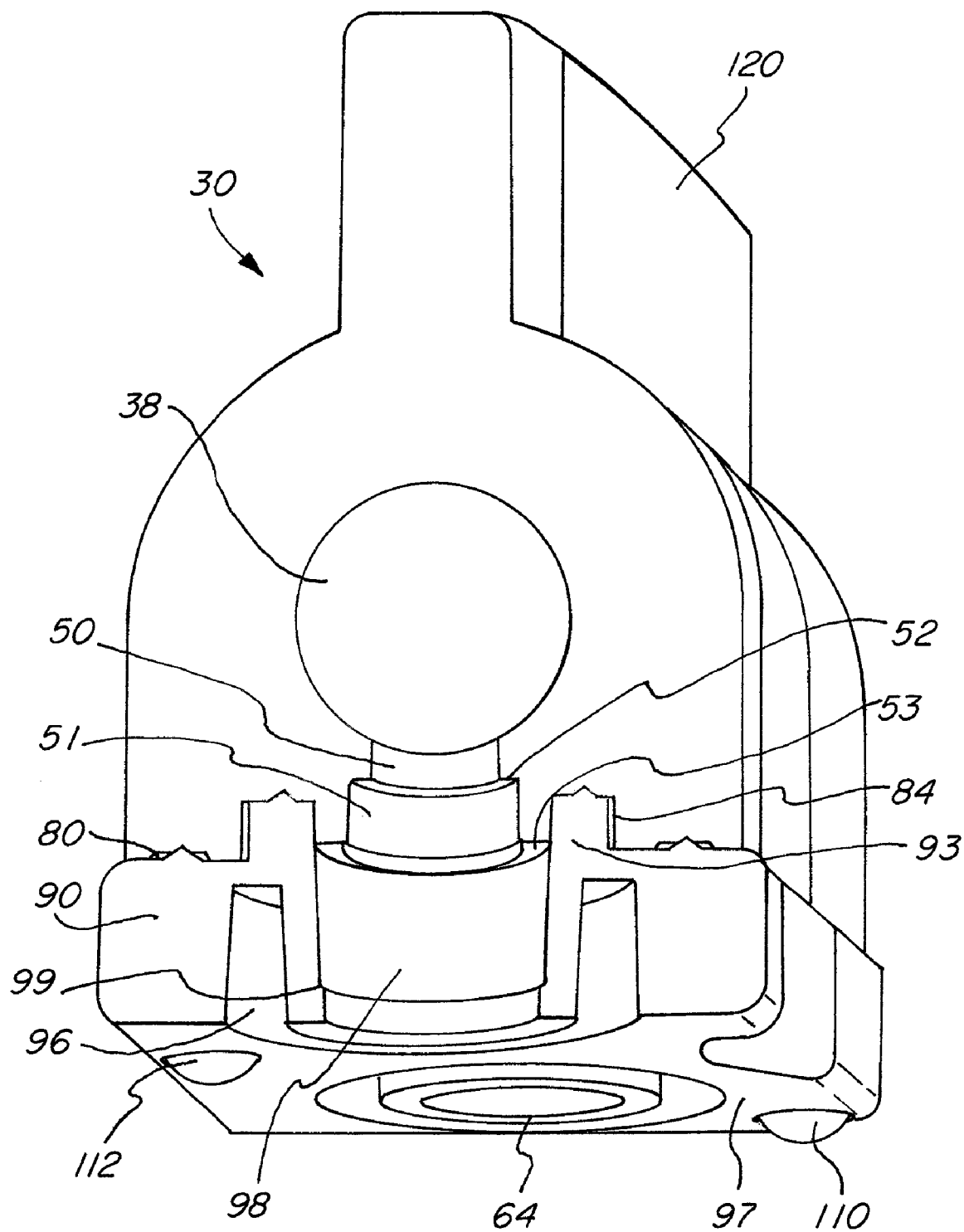
FIG. 2 shows a fluid chamber with an inventive pressure measurement device in cross-section.
Figure 3:
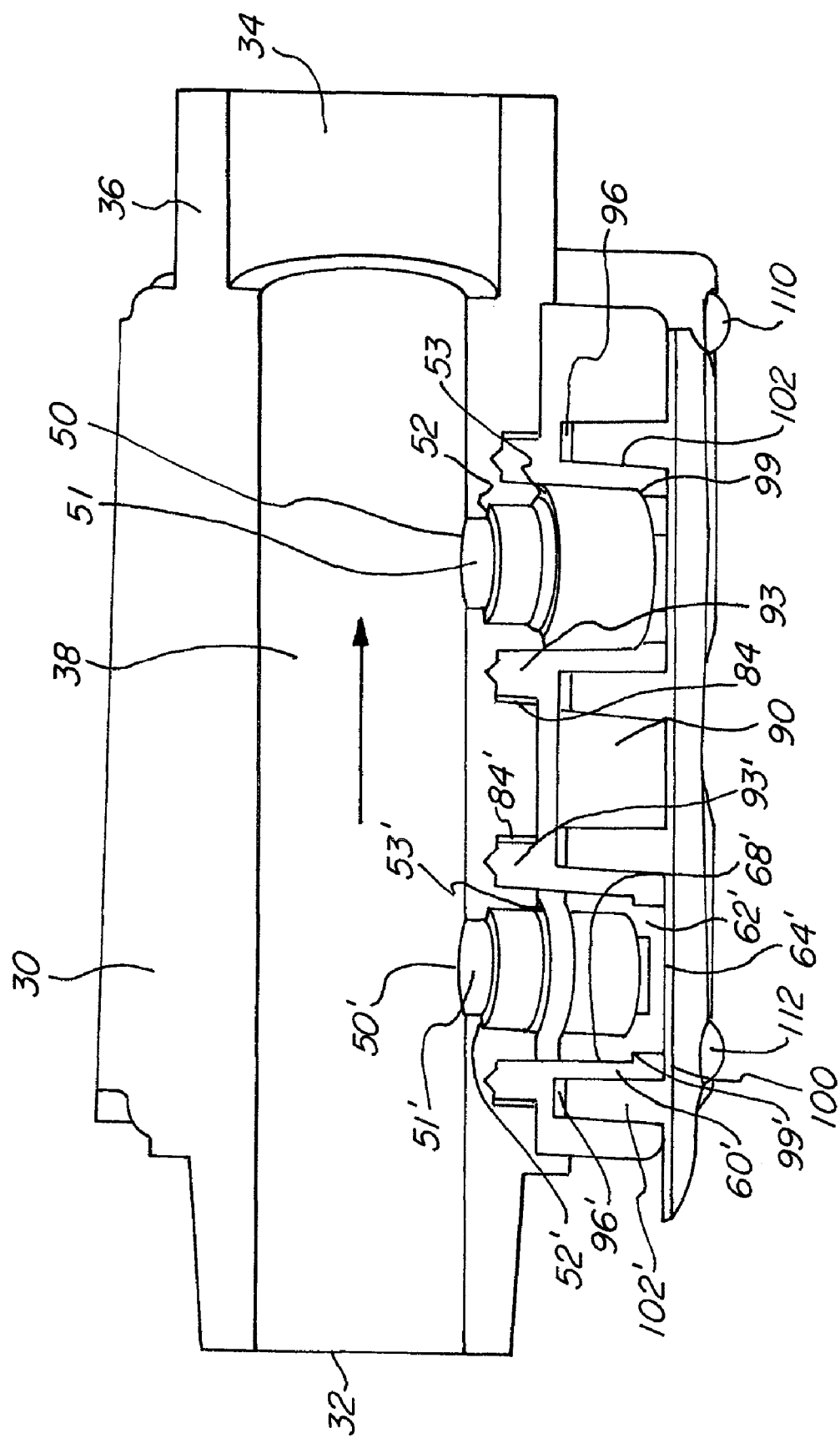
FIG. 3 shows a fluid chamber with connected fluid line, transmission element, and insulating membrane of an inventive pressure measurement device.
Figure 4:
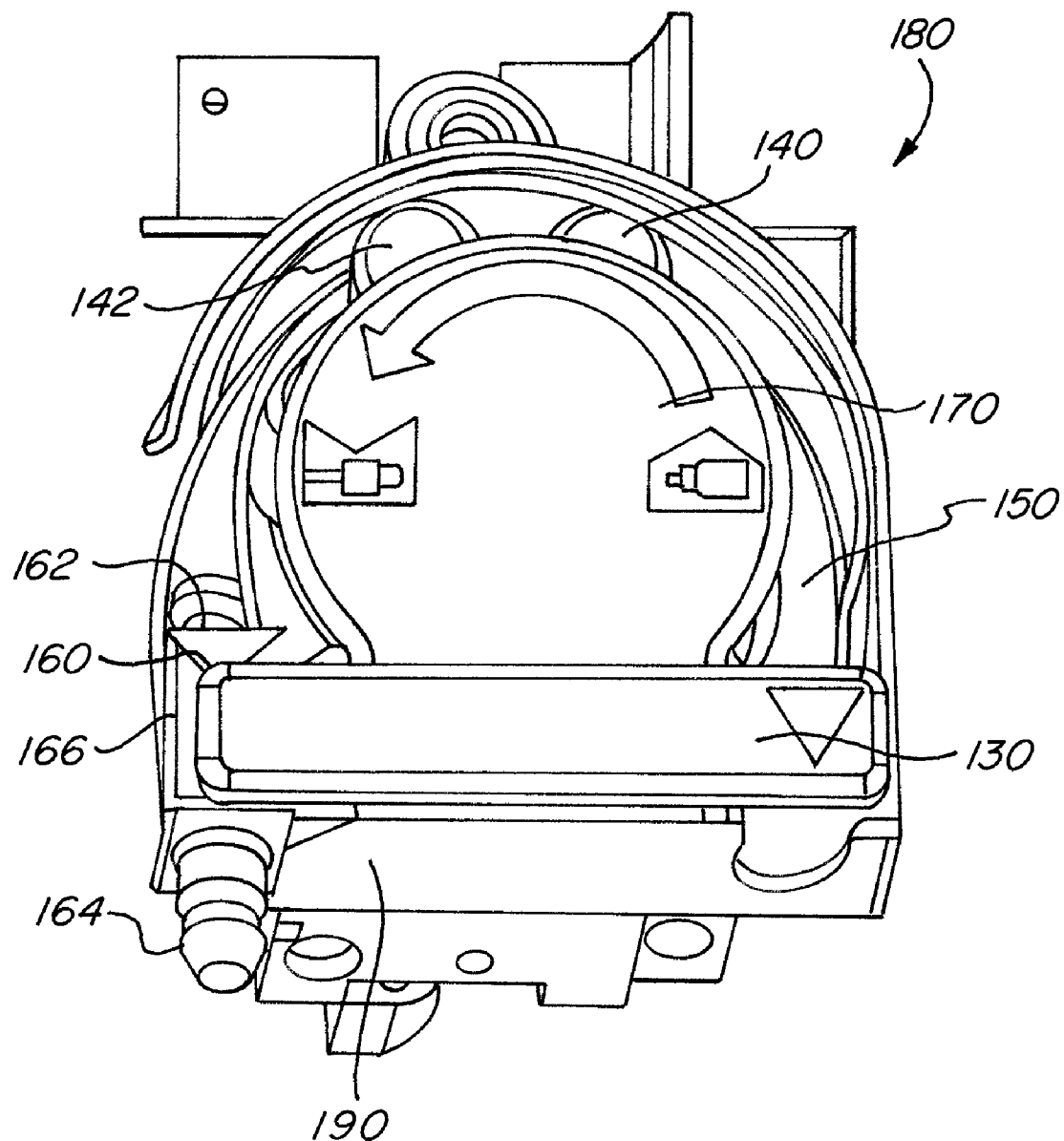
FIG. 4 shows an inventive device, which is positioned for appropriate use in a roller pump.

The first illustration, FIG. 1, depicts in longitudinal section an inventive device, labeled with the common reference number 10, for measuring pressure in a fluid line 20. Additional details of the pressure-measuring device 10 are shown in FIGS. 2 and 3, with components that are identical, of the same type, or comparable to one another are designated with the same reference numbers. Reference numbers with prime (') re used to designate components presented as duplicates in identical realization as the components bearing the non-prime reference numbers. FIG. 4 shows an inventive device in connection with a roller pump, as it is customarily used in clinical practice.

The pressure-measuring device 10 comprises a fluid chamber 30 that is configured as a flow-through chamber. The fluid chamber 30 is dissolubly connected at the fluid ingress end 32 and at the fluid egress end 34 with a fluid line 2-. The fluid line 20 takes the form of a synthetic hose that is mounted onto the connection 36 of the fluid chamber 30 and is form-locked together with the fluid egress end 34.

The interior 38 of the fluid chamber 30 comprises, besides the fluid ingress end 32 and fluid egress end 34, two additional openings 50, 50' to branch lines 51, 51', which are positioned in the wall of the fluid chamber 30 longitudinally aligned with the direction of flow of the fluid, which is indicated by the direction of the arrow in FIG. 1.

Springs 70, 70' of the transmission elements 60, 60' are supported on ring-shaped abutment surfaces 52, 52' in the branch lines 51, 51'. The springs 70, 70' are contiguous with the ring-shaped abutment surfaces 66, 66' in the piston-shaped elements 62, 62' of the transmission elements 60, 60'. The piston-shaped elements 62, 62' are positioned mobilely between the ring-shaped abutment surfaces 53, 53' and the ring-shaped abutment surfaces 99, 99' of a base plate 90. The piston-shaped elements 62, 62' comprise protrusions 68, 68'. Said protrusions 68, 68' configure abutment surfaces that overlap with the abutment surfaces 99, 99' of the base plate, so that the stroke of the motion of the piston-shaped elements 62, 62' is restricted and the transmission elements 60, 60' are retained in the passage 98, 98' of the base plate 90.

The springs 70, 70' of the transmission elements 60, 60' are selected so that, when expanded, their length is greater than the distance between the abutment surfaces 52, 52' and the abutment surfaces 99, 99'.

The branch lines 51, 51' and connecting passages 98, 98' of the base plate 90 are filled with the fluid. The piston-shaped elements 62, 62' are also filled with fluid and can be rinsed by the fluid on the outside. The piston-shaped elements can include perforations or bored openings (not illustrated) that make possible a homogeneous distribution of fluid in the passages 98, 98' and thus of the fluid pressure.

The piston-shaped elements 62, 62' of the transmission elements 60, 60' are impacted with the pressure of the fluid and of the pre-tensing of the springs 70, 70'. The ends 64, 64' of the transmission elements 60, 60' act on a membrane 100, which they impact at a pressure that essentially proportionately encompasses the pre-tensing of the springs 70, 70' and the fluid pressure.

The membrane 100 surrounds the ends 64, 64' of the transmission elements 60, 60' and forms a liquid-tight lock by which any leakage or seepage of fluid from the fluid line 20, the interior 38 of the fluid chamber 30, the branch lines 51, 51', and the passages 98, 98' is prevented.

In FIG. 2 the structure of the fluid chamber 30 is shown in cross-section. The interior of the fluid chamber comprises an opening 50 to a branch line 51. The branch line comprises a ring-shaped abutment surface 52. The circular-shaped abutment surface 52 serves as a supporting surface for a spring 70 (not illustrated).

The fluid chamber 30 comprises ring-shaped recesses 84, 84'. After mounting the spring on the abutment surface 52 of the branch line 51 and the piston-shaped element 62 on the abutment surface 53 of the branch line 51, the axial area of motion of the transmission element 60 is secured in the passage 98 of a base plate 90 because the passage 98 comprises a ring-shaped abutment surface 99.

The base plate 90 comprises ring-shaped protrusions 93, 93' which engage in recesses 84, 84' of the fluid chamber 30. By ultrasonic welding, a flush connection can be produced between the fluid chamber 30 and the base plate 90, each of which is made of synthetics such as polyethylene or polypropylene. As a result, the transmission element 60 is lodged in the passage 98 of the base plate 90 between the abutment surfaces 52 and 99.

The end 64 of the transmission element 60 facing the transducer 40 forms an approximately flush terminal point with the underside 97 of the base plate 90.

On its underside 97 the base plate 90 comprises circular-shaped recesses 96, 96'. FIG. 3 shows that the recesses 96, 96' are positioned approximately concentrically around the passages 98, 98' of the base plate 90.

The membrane 100, which is made of silicon, for instance, and is sterile, comprises circular protrusions 102, 102' that fit in a form-locking connection in the recesses 96, 96' of the base plate 90. The membrane 100 as a result can be positioned especially easily and can be combined with the base plate.

The membrane 100 forms a fluid-tight lock of the base plate 90 and comprises an approximately flat outer surface that is in power-locking connection (see also FIG. 1) with the membranes 42, 42' of the housings 41, 41' of the transducers 40, 40'.

The walls 46 and 48' of the housings 41, 41' are inserted in recesses 45, 45' of the plate 46. The transducers 40, 40' are positioned on the plate 46, which can be configured as a circuit board with imprinted switching circuits. The transducers 40, 40' can be imprinted or etched, for instance, onto the plate 46 as switching circuits.

The interiors of the housings 41, 41' are filled with silicon 43, which serves to retransmit the pressure from the membranes 41, 41' to the transducers 40, 40'. The pre-tensing with which the membranes 41, 41' are impacted prevents displacement of the silicon filling 43 in the housings 41, 41', which could cause a drift in the registering of pressure by the transducers 40, 40'.

The base plate includes feet 110, 112, 114 that are hemispherical in shape. FIG. 4 shows a connecting element (connector) 160 consisting of an ultrasonically welded fluid chamber 30 with base plate 90. After inserting the membrane 100 in the base plate 90, the feet 110, 112, 114 serve to position the connecting element 160 in the housing 190 of a roller pump 180. For this purpose the housing 190 comprises corresponding troughs (not illustrated) in the hose bed 150, which serve to receive the semispherical feet 110, 112, 114.

On the outer wall 166 the connecting element 160 comprises a groove (not illustrated) that simplifies the exact insertion of the connecting element 160 in the hose bed 150 of the housing 190 of the roller pump 180.

By means of a rotary lever 140 the connecting element 160 is locked in the hose bed 150 of the roller pump 180. The lever 130 presses on the ridge 120 of the fluid chamber 30 and causes a power lock between the base plate 90 and the housing 190 of the roller pump 180. The lever 130 exerts a force on the fluid chamber 30 that corresponds to a multiple of the sum of the pre-tensing and pressure of the fluid.

The connecting element 160 comprises connections 162 and 164. The connection 162 serves to connect a hose segment of preferably resistant synthetic material (not illustrated) to the connecting element 160. By means of the rollers 140 and 142 (and four additional rollers, not illustrated), which are positioned on a roller head 170, the non-illustrated hose segment is pressed in or squeezed so that upon rotation of the roller head 120 a peristaltic action is achieved that is used to convey the fluid.

The connection 164 serves to connect an additional synthetic hose of a hose assembly that serves as supply line of the fluid.

What is claimed is:

1. A device for measuring pressure in a fluid line, with a fluid chamber, which forms a flow-through connection with the fluid line, and with a transducer, characterized in that the fluid chamber comprises an opening to a branch line and in the branch line of the fluid chamber at least one end of a transmission element is inserted and the transmission element forms a power-locking connection between the fluid chamber and the transducer, and the transmission element is suited for transmitting the fluid pressure to the transducer.

2. The device according to claim 1, wherein the fluid chamber is configured as a flow-through chamber.

3. The device according to claim 2, wherein the fluid ingress end of the flow-through chamber and the fluid egress end of the flow-through chamber are dissolubly connected with the fluid line.

4. The device according to claim 1, wherein the transmission element is impacted with a pre-tensing.

5. The device according to claim 4, wherein the pre-tensing with which the transmission element is impacted is configured so that it can be adjusted.

6. The device according to claim 1, wherein the transmission element is piston-shaped.

7. The device according to claim 1, wherein the transmission element is provided with at least one spring assembly or with at least one magnetic arrangement that is suited for creating a pre-tensing.

8. The device according to claim 1, wherein the transmission element is of unit configuration.

9. The device according to claim 1, wherein the transmission element is configured of several parts.

10. The device according to claim 1, wherein the transmission element is configured as replaceable.

11. The device according to claim 1, wherein the end of the transmission element facing the transducer is surrounded by a membrane so that a fluid-tight lock of the branch line of the fluid chamber is configured with the end of the transmission element facing the transducer.

12. The device according to claim 1, wherein the branch line of the fluid chamber, into which the at least one end of the transmission element is inserted, is locked fluid-tight by an insulating ring or a membrane.

13. The device according to claim 1, wherein the end of the transmission element inserted into the branch line of the fluid chamber is mounted by a silicon oil so that it glides and by means of an insulating element forms a fluid-tight lock of the branch line.

14. The device according to claim 1, wherein the device comprises several transmission elements and several transducers and a fluid chamber with several openings to several branch lines.

15. The device according to claim 14, wherein at least one membrane is provided which forms a fluid-tight lock of the several branch liens of the fluid chamber and the lock keeps the interior of the fluid chamber sterile.

16. The device according to claim 1, wherein the outer walls of the fluid chamber comprise at least one recess that is suited as a positioning aid.

* * * * *